(12) United States Patent
Nilson et al.

(10) Patent No.: US 6,322,542 B1
(45) Date of Patent: Nov. 27, 2001

(54) DEVICE FOR DELIVERING LIQUID CONTAINING MEDICAMENT

(75) Inventors: Billy Nilson, Mjölby; Arne Eek, Trosa, both of (SE)

(73) Assignee: AstraZeneca AB (SE)

( * ) Notice: Subject to any disclaimer, the term of this patent is extended or adjusted under 35 U.S.C. 154(b) by 0 days.

(21) Appl. No.: 09/254,421

(22) PCT Filed: Dec. 15, 1998

(86) PCT No.: PCT/SE98/02318

§ 371 Date: Mar. 8, 1999

§ 102(e) Date: Mar. 8, 1999

(87) PCT Pub. No.: WO99/32185

PCT Pub. Date: Jul. 1, 1999

(30) Foreign Application Priority Data

Dec. 19, 1997 (SE) .................................................. 9704769

(51) Int. Cl.[7] .................................................. A61M 5/00
(52) U.S. Cl. .................. 604/257; 604/261; 604/275; 604/912
(58) Field of Search .............................. 604/207, 48, 142, 604/153, 257, 261, 275, 912; 417/474, 477.1, 93.01

(56) References Cited

U.S. PATENT DOCUMENTS

| | | | |
|---|---|---|---|
| 4,312,344 | 1/1982 | Nilson | 128/216 |
| 4,405,308 | 9/1983 | Jessup | 604/200 |
| 4,548,607 | * 10/1985 | Harris . | |
| 4,699,615 | * 10/1987 | Fishell et al. . | |
| 4,886,493 | 12/1989 | Yee | 604/54 |
| 4,898,583 | * 2/1990 | Borsanyi et al. . | |
| 4,898,585 | * 2/1990 | Borsanyi et al. . | |
| 4,950,231 | * 8/1990 | Liu . | |
| 5,053,031 | * 10/1991 | Borsanyi . | |
| 5,061,243 | * 10/1991 | Winchell et al. . | |
| 5,085,644 | * 2/1992 | Watson et al. . | |
| 5,152,753 | * 10/1992 | Laguette et al. . | |
| 5,232,448 | * 8/1993 | Zdeb . | |
| 5,284,132 | 2/1994 | Geier | 128/200.22 |
| 5,419,772 | * 5/1995 | Teitz et al. . | |
| 5,707,361 | * 1/1998 | Slettenmark . | |
| 5,766,157 | * 6/1998 | Tilton, Jr. . | |
| 5,840,076 | * 11/1998 | Swanson et al. . | |

FOREIGN PATENT DOCUMENTS

| | | | |
|---|---|---|---|
| 505 330 | 9/1992 | (EP) | A61M/5/32 |
| WO 97/06842 | 2/1997 | (WO) | A61M/15/00 |
| WO 95/04563 | 2/1995 | (WO) | A61M/5/315 |

OTHER PUBLICATIONS

The International Search Report for PCT/US98/02318, filed by applicants on Dec. 15, 1998.

* cited by examiner

Primary Examiner—Richard K. Seidel
Assistant Examiner—Kevin C. Sirmons
(74) Attorney, Agent, or Firm—Michael A. Sanzo; Pillsbury Winthrop LLP

(57) ABSTRACT

A delivery means for delivering liquid containing medicament to a posterior region of the nasal cavity, comprising an elongate tubular member (35; 151) and a nozzle (37; 153) at the free end thereof, which nozzle (37; 153) includes at least one opening (39; 155) through which liquid is in use delivered.

22 Claims, 7 Drawing Sheets

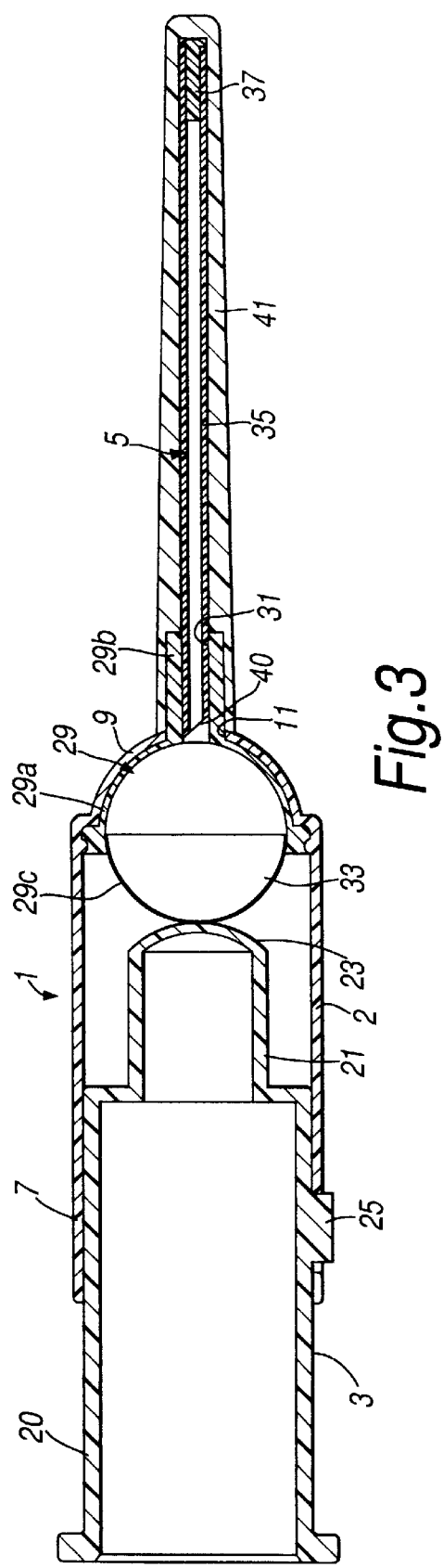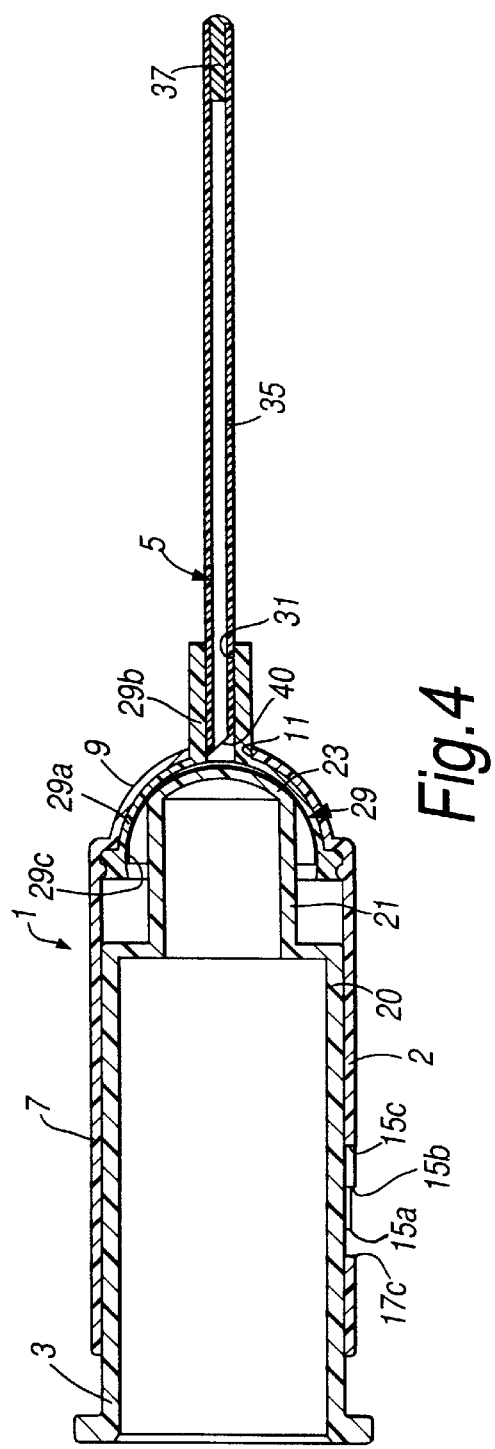

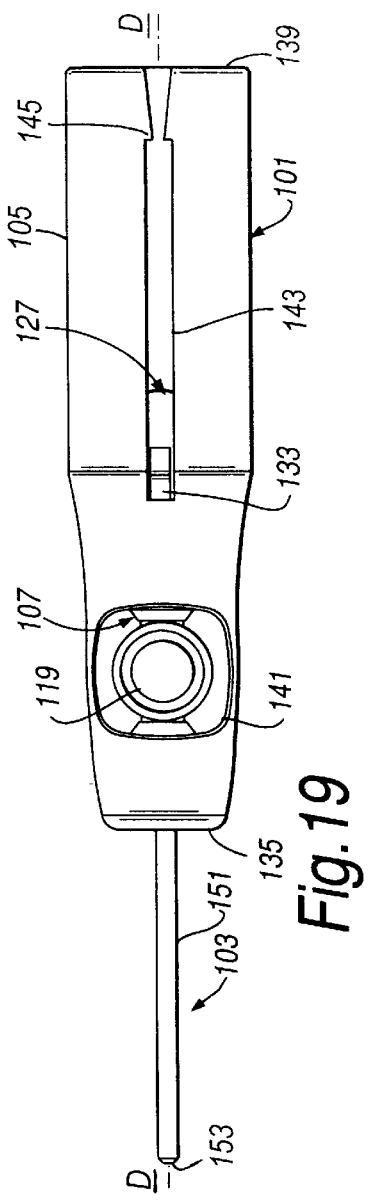
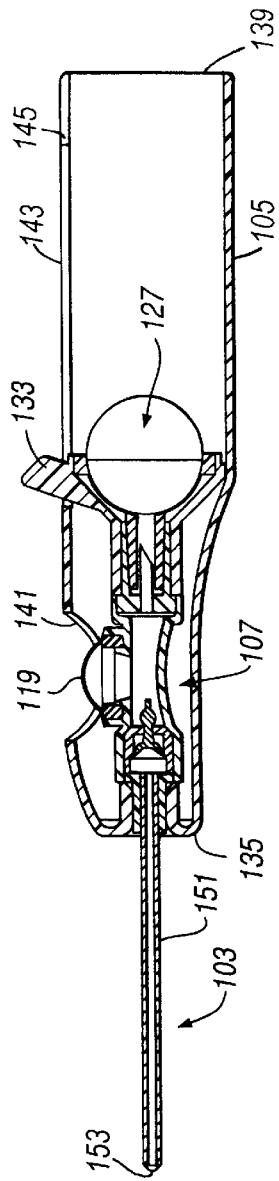
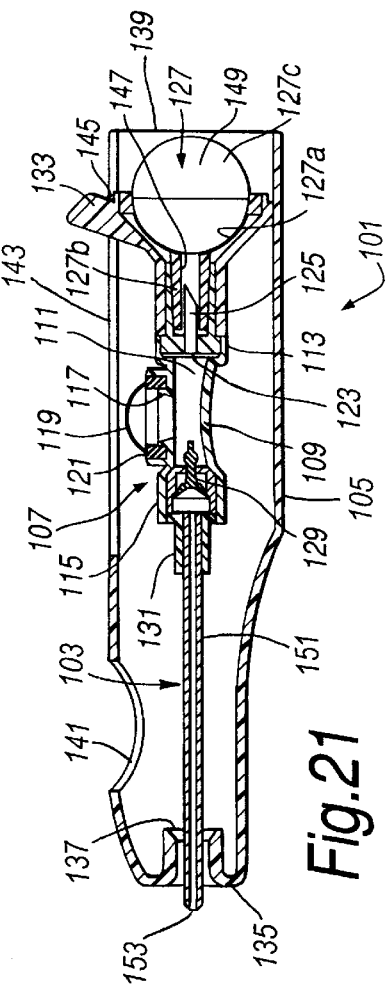

DEVICE FOR DELIVERING LIQUID CONTAINING MEDICAMENT

The present application represents U.S. national stage of international application PCT/SE98/023138 with an international filing date of Dec. 15, 1998, and which was published in English under Article 21(2) of the PCT on Jul. 1, 1999. The international application claims priority to Swedish application 9704769-0, which was filed on Dec. 19, 1997.

FIELD OF THE INVENTION

The present invention relates to a delivery means for and a method of delivering liquid containing medicament to a posterior region of the nasal cavity, in particular the delivery of local anaesthetic in the treatment of vascular headache.

BACKGROUND OF THE INVENTION

U.S. Pat. No. 4886493 discloses an applicator for the delivery of local anaesthetic to the sphenopalatine ganglion, which applicator comprises a flexible tube, one end of which is open and in use located adjacent the sphenopalatine ganglion and through the other end of which a metered volume of local anaesthetic in the form of a spray is passed. This applicator, whilst delivering a metered volume of local anaesthetic to the sphenopalatine ganglion, still, however, does not completely effectively deliver the local anaesthetic.

It is an aim of the present invention to provide a delivery means for delivering medicament more effectively to a posterior, in particular the posterior most, region of the nasal cavity. In this way, more immediate effect will be obtained and the user will be required less often to re-administer medicament to achieve the effect, which over delivery can lead to side effects.

SUMMARY OF THE INVENTION

The present invention provides a delivery means for delivering liquid containing medicament to a posterior region of the nasal cavity, comprising an elongate tubular member and a nozzle at the free end thereof, which nozzle includes at least one opening through which liquid is in use delivered. The delivery means finds particular application in the delivery of local anaesthetic, such as Xylocaine®, for the treatment of vascular headache, especially migraine.

The present invention also extends to a delivery device which incorporates the above-described delivery means.

In one embodiment the delivery device includes a delivery unit for delivering a plurality of metered volumes of liquid containing medicament to the delivery means, which delivery unit comprises a main body including a barrel and a plunger axially movable within the barrel, wherein one of the barrel and the plunger includes at least one path and the other of the barrel and the plunger includes at least one projection which is movable along the at least one path, the at least one path having an axially forward surface, in the direction of movement of the at least one projection through the at least one path in the delivery of liquid, which defines a plurality of axially-spaced steps at which the at least one projection is locatable.

In another embodiment the delivery device includes a delivery unit for delivering one or more metered volumes of liquid containing medicament to the delivery means, which delivery unit comprises a pump assembly on the actuation of which a metered volume of liquid is delivered to an outlet thereof. Preferably, the pump assembly comprises a main body which defines a chamber having a first opening that defines an inlet, a second opening that defines an outlet and a third opening across which a resilient membrane is disposed, delivery of a metered volume of liquid to the outlet being achieved by movement of the membrane.

The present invention further provides a method of delivering liquid containing medicament to a posterior region of the nasal cavity, comprising the steps of inserting a delivery means comprising an elongate tubular member and a nozzle at the free end thereof, which nozzle includes at least one opening, into one of the nasal passages so as to locate the nozzle near a posterior region of the nasal cavity and delivering liquid through the at least one opening in the nozzle.

In preferred embodiments the delivery means and the method of the present invention are used to deliver liquid containing medicament to the pterygopalatine fossa and the surrounding pharyngeal and nasal area delineated by proximally situated so orbitale and distally os maxillaris.

The present invention yet further provides a delivery device for delivering a plurality of metered volumes of liquid containing medicament, comprising a delivery means as an elongate tubular member through which liquid containing medicament is in use delivered and a delivery unit coupled to the delivery means, which delivery unit comprises a main body including a barrel and a plunger axially movable within the barrel, wherein one of the barrel and the plunger includes at least one path and the other of the barrel and the plunger includes at least one projection which is movable along the at least one path, the at least one path having an axially forward surface, in the direction of movement of the at least one projection through the at least one path in the delivery of liquid, which defines a plurality of axially-spaced steps at which the at least one projection is locatable.

The present invention still further provides a delivery device for delivering one or more metered volumes of liquid containing medicament, comprising a delivery means through which liquid containing medicament is in use delivered and a delivery unit coupled to the delivery means, which delivery unit comprises a pump assembly on the actuation of which a metered volume of liquid is delivered to the delivery means and a housing in which the delivery means and the pump assembly are slideably disposed, wherein the delivery means is movable between a first position in which the delivery means is substantially within the housing and a second position in which the delivery means is extended from the housing in a position ready for use.

Preferred embodiments of the present invention will now be described hereinbelow by way of example only with reference to the accompanying drawings, in which:

BRIEF DESCRIPTION OF THE DRAWINGS

FIG. 3 illustrates a diametric sectional view (along section A—A in FIG. 2) of the delivery device of FIG. 1 before use;

FIG. 4 illustrates a diametric sectional view (along section B—B in FIG. 2) of the delivery device of FIG. 1 after use;

FIG. 19 illustrates a plan view of the delivery device of FIG. 18 in the in use position;

FIG. 20 illustrates a vertical sectional view (along section D—D in FIG. 19) of the delivery device of FIG. 18 in the in use position;

FIG. 21 illustrates a vertical sectional view (along section D—D in FIG. 19) of the delivery device of FIG. 18 in the closed or storage position;

FIG. 1 illustrates a first delivery device which comprises a delivery unit 1, in this embodiment a syringe, comprising a main body 2 and a plunger 3 which is axially displaceable within the main body 2, and a delivery means 5 from which liquid is in use delivered.

DETAILED DESCRIPTION OF THE INVENTION

Figure 1:
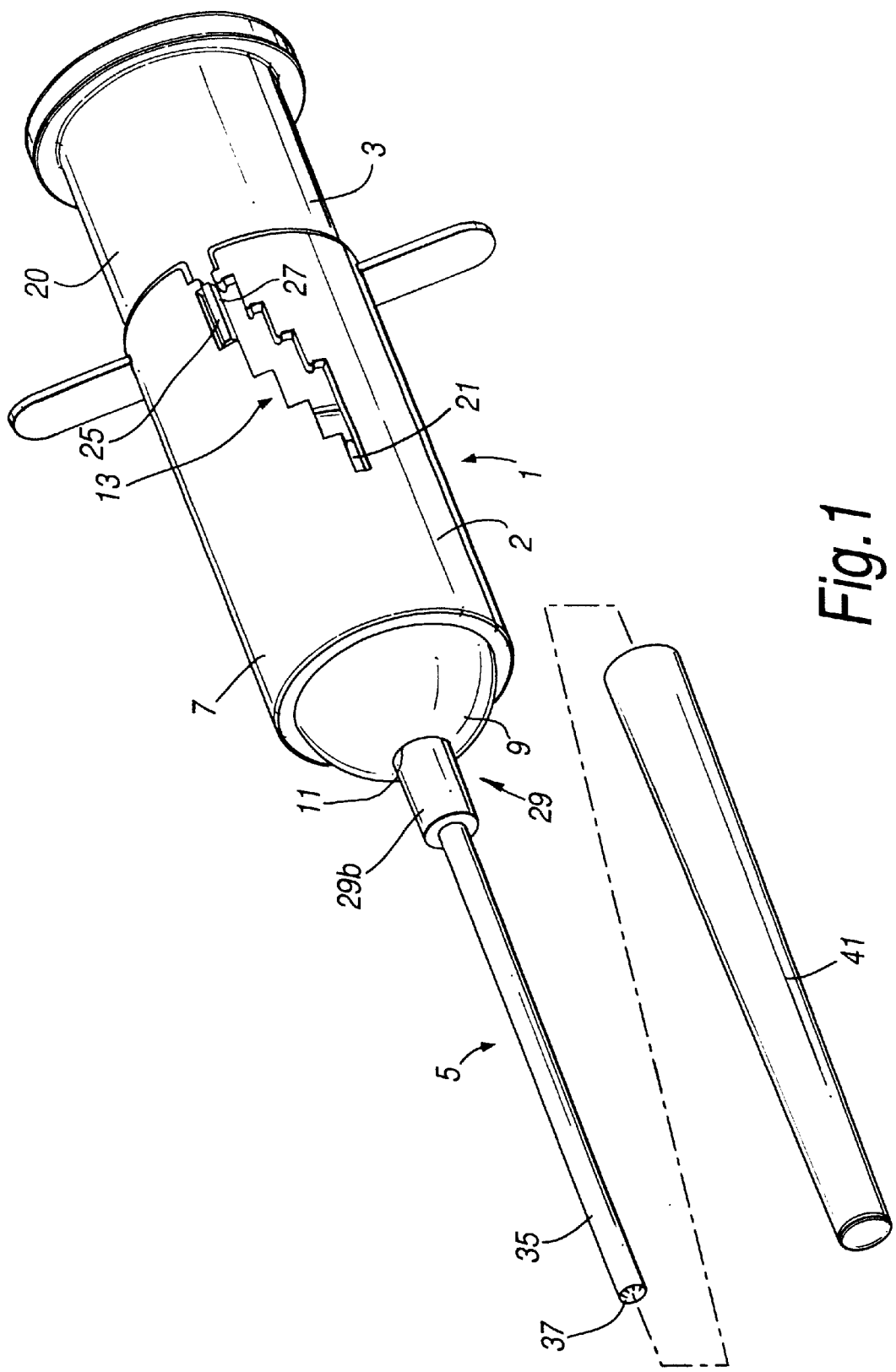
FIG. 1 illustrates a perspective view of a first delivery device incorporating a delivery means in accordance with a first embodiment of the present invention.
Figure 2:
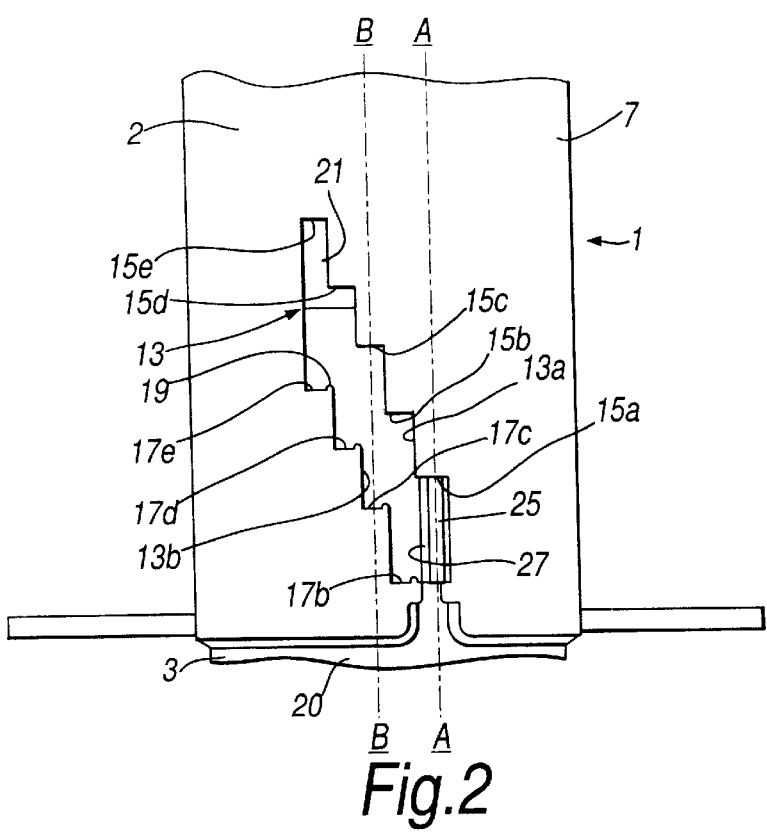
FIG. 2 illustrates in enlarged scale a side view of a part of the main body and the plunger of the delivery unit of the delivery device of FIG. 1.
Figure 5:
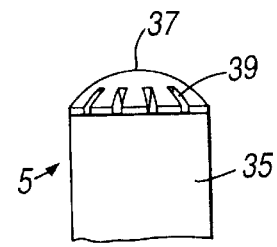
FIG. 5 illustrates in enlarged scale a side view of the distal end of the delivery means of the delivery device of FIG. 1.
Figure 6:
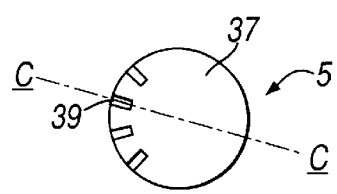
FIG. 6 illustrates an end view of the distal end of the delivery means of FIG. 5.
Figure 7:
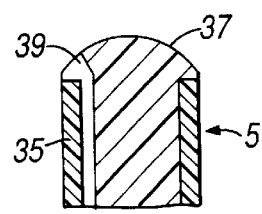
FIG. 7 illustrates a diametric sectional view (along section C—C in FIG. 6) of the distal end of the delivery means of FIG. 5.

The main body 2 comprises a cylindrical barrel 7 and a wall member 9, in this embodiment part-spherical in shape, at one end thereof. In this embodiment the main body 2 is formed of a plastics material, preferably polyethylene or polypropylene. The end wall member 9 has an opening 11 therein which is co-incident with the longitudinal axis of the barrel 7. The other end of the barrel 7 is open and receives the plunger 3. The peripheral wall of the barrel 7 includes a path 13 which extends from the open end thereof, in this embodiment in an anti-clockwise sense. In this embodiment the path 13 is defined by a through slot. It will, however, be appreciated by a person skilled in the art that the path 13 could alternatively be defined by a blind slot in the inner surface of the barrel 7. The path 13 has an axially forward surface 13a that defines a plurality of axially-spaced steps 15a–15e. In this embodiment the path 13 also has an axially rearward surface 13b that defines a plurality of axially-spaced steps 17b–17e which are symmetrical, but axially-shifted, in relation to the steps 15a–15e defined by the forward surface 13a of the path 13. The steps 17b-17e defined by the rearward surface 13b of the path 13 each have a detent 19 formed thereon at the trailing edge relative to the sense of rotation of the plunger 3, anti-clockwise in this embodiment. The detents 19 are configured to prevent back rotation of the plunger 3, but not impede axial movement of the plunger 3 relative to the barrel 7. In another embodiment, where the delivery device is to be reusable, the detents 19 can be omitted, thereby allowing withdrawal of the plunger 3 from the barrel 7.

The plunger 3 comprises a first part 20, which is dimensioned so as to be a free but not loose fit within the barrel 7, and a second part 21, which is of smaller radial dimension than the first part 20, at the distal end of the plunger 3 as acted upon by the user. In this embodiment the plunger 3 is formed of a plastics material, preferably polyethylene or polypropylene. The distal end of the second part 21 is formed as a part-spherical surface 23. The plunger 3 further comprises a projection 25 which extends axially to and projects radially from the first part 20 thereof. The projection 25 is configured to travel in the path 13. The projection 25 has a chamfered longitudinal edge 27, which edge 27 is the forward edge relative to the sense of rotation of the plunger 3 in use. The chamfered edge 27 enables the projection 25 to pass each respective detent 19 on rotation of the plunger 3 in the operative sense, in this embodiment in the anti-clockwise sense. The plunger 3 is prevented from being back rotated in the opposite sense by the detents 19 which engage the projection 25.

The delivery unit 1 further comprises a container 29 which is fitted, in this embodiment clipped, within the main body 2 to the end wall member 9 thereof. The container 29 comprises a first, rigid hemi-spherical part 29a, which corresponds in shape to the shape of the end wall member 9 of the main body 2, a second, shank part 29b, which extends axially from the first part 29a through the opening 11 in the end wall member 9 of the main body 2 and has an elongate bore 31 that is configured to receive the delivery means 5, and a third, deformable hemispherical part 29c, which with the first part 29a defines a spherical chamber 33 that contains a volume of liquid for delivery. In a reusable delivery device a used container 29 can be removed from the delivery unit 1 and replaced by a new container 29. The material of the container 29 is selected according to the contained liquid; it being necessary for the material to be inert to the contained liquid. Typical materials include polyethylene and polypropylene. In this embodiment, prior to fitting of the delivery means 5, the distal end of the shank part 29b of the container 29 is closed by a film (not illustrated), preferably of a plastics material such as polyethylene or polypropylene, which acts to enclose the liquid in the container 29. The third part 29c of the container 29 is configured to collapse as pressure is applied thereto by the plunger 3, thereby passing liquid into and through the delivery means 5. In this regard, it will be noted that as the chamber 33 of the container 29 is spherical in shape, the radius of curvature of the part-spherical surface 23 of the second part 21 of the plunger 3 is such that a uniform volume of liquid is provided on each axial movement of the plunger 3.

The delivery means 5 comprises an elongate tubular member 35 and a nozzle 37 at the distal end thereof, which nozzle 37 includes a plurality of openings 39 arranged to eject liquid therefrom in a focused pattern. The other end of the tubular member 35 which fits into the shank part 29b of the container 29 is angled so as to provide a cutting edge 40 capable of penetrating the film which closes the distal end of the shank part 29b. In a preferred embodiment the tubular member 35 is flexible and comprises one of polyethylene or polypropylene. The tubular member 35 preferably has a length of about 40 mm, an outer diameter of from 1 to 2 mm and a wall thickness of about 0.1 mm. In this embodiment the nozzle 37 is provided by an insert which is of circular section and has a part-spherical distal end, with the openings 39 being located at the periphery over a sector of about 90 degrees. Further, in this embodiment the nozzle 37 is formed of a plastics material, such as polyethylene or polypropylene. The outer surface of the tubular member 35 is preferably coated with a hydrophilic material, such as polyvinyl pyrrolidone, which is wet before use so as thereby to reduce the frictional resistance on contact with body tissue. In a preferred embodiment the tubular member 35 is provided with an indicating means (not illustrated) which extends radially therefrom in the direction in which liquid is in use ejected from the openings 39. Such an indicating means enables a user readily to determine the direction in which liquid will be ejected from the delivery means 5.

The delivery device further comprises a sheath 41 for protecting the delivery means 5. The sheath 41 is tubular, with one end closed and the other end open for fitting on the shank part 29b of the container 29. In this embodiment the sheath 41 is formed of a plastics material, preferably polyethylene or polypropylene. The open end of the sheath 41 is configured to be a hermetic fit with the shank part 29b of the container 29 so as to allow the sheath 41 to be readily removed and replaced as necessary during the lifetime of the delivery device.

Figure 8:
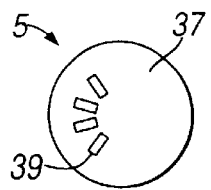
FIGS. 8 to 15 illustrate in enlarged scale end views of the distal ends of delivery means in accordance with second to ninth embodiments of the present invention.
Figure 9:
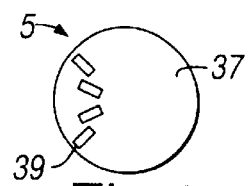
Figure 10:
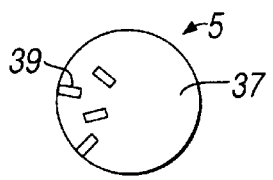
Figure 11:
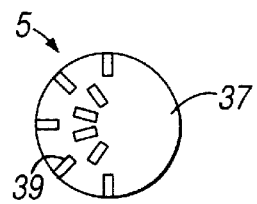
Figure 12:
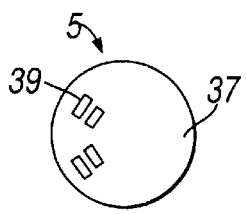
Figure 13:
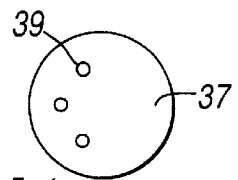
Figure 14:
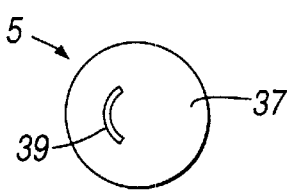
Figure 15:
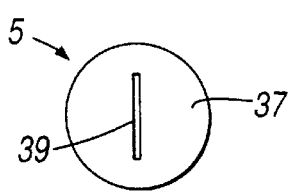

FIGS. 8 to 15 illustrate the distal ends of delivery means 5 in accordance with second to ninth embodiments of present invention. In FIG. 8, the openings 39 are radially-directed elongate slots located on a circle whose radius is less than that of the radius of the nozzle 37, with the openings 39 being located over a sector of about 90 degrees. In FIG. 9, the openings 39 are radially-directed elongate slots which are staggered, with the openings 39 being located over a sector of about 90 degrees on circles having different radii but radii smaller than that of the radius of the nozzle 37. In FIG. 10, the openings 39 are radially-directed elongate slots which are again staggered and again located over a sector of about 90 degrees, but with first openings 39 being located at the periphery of the nozzle 37 and second openings 39 being located on a circle whose radius is smaller than that of the radius of the nozzle 37. In FIG. 11, the openings 39 are radially-directed elongate slots which are located in similar radial positions to the openings 39 in the nozzle 37 of FIG. 10, but extend over a sector of about 180 degrees. In FIG. 12, the openings 39 are elongate slots located over a sector of about 90 degrees in similar radial positions to the openings 39 in the nozzle 37 of FIG. 9, but are circularly-directed as opposed to radially-directed. In FIG. 13, the openings 39 are circular and are located over a sector of about 120 degrees on a circle whose radius is smaller than that of the radius of the nozzle 37. In FIG. 14, the nozzle 37 includes a single arcuate opening 39 in the form of a slot located over a sector of about 90 degrees on a circle whose radius is smaller than that of the radius of the nozzle 37. In FIG. 15, the nozzle 37 includes a single diametrically-directed elongate opening 39 in the form of a slot.

Figure 16:
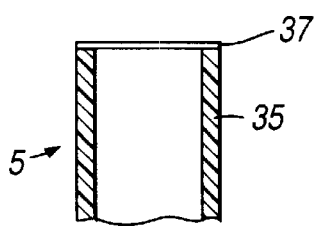
FIG. 16 illustrates in enlarged scale a diametric sectional view of the distal end of a delivery means in accordance with a tenth embodiment of the present invention.
Figure 17:
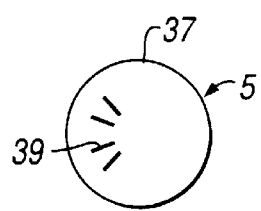
FIG. 17 illustrates an end view of the distal end of the delivery means of FIG. 16.

FIGS. 16 and 17 illustrate the distal end of a delivery means 5 in accordance with a tenth embodiment of the present invention. In this embodiment the nozzle 37 comprises a film adhered to the distal end of the tubular member 35. The nozzle 37 includes a plurality of openings 39 which are in the form of radially-directed slits. In this embodiment, as in the embodiment of FIG. 8, the openings 39 extend over a sector of about 90 degrees. The nozzle 37 is preferably formed from a resilient material, typically a plastics material such as polyethylene or polypropylene. Where the nozzle 37 is formed of a plastics material the adhesion is preferably achieved by heat melting.

In use, the user takes the delivery device loaded typically with a local anaesthetic, such as Xylocaine®, as illustrated in FIG. 3 and removes the sheath 41 from around the delivery means 5. The user then wets the hydrophilic coating on the tubular member 35 of the delivery means 5 and passes the same into one of his/her nasal passages. The distal end of the delivery means 5, which includes the nozzle 37, is located typically adjacent aposterior region of the nasal cavity. Where the nozzle 37 includes openings 39 on only one side, the user ensures that side of the nozzle 37 in which the openings 39 are located is directed towards the site to which the liquid is to be applied. When the delivery means 5 is fully inserted, the user then operates the delivery device to eject a metered volume of liquid from the delivery means 5. Operation of the delivery device requires two distinct steps, these being firstly rotation of the plunger 3, in an anti-clockwise sense in the described embodiments, relative to the main body 2 to prime the delivery device, and secondly depression of the plunger 3 to eject liquid from the delivery means 5. In preferred embodiments the delivery device is configured such that movement of the plunger 3 axially between two adjacent forward steps, for example from step 15a to step 15b, causes a volume of liquid of from 100 to 250 µl to be ejected from the delivery means 5. The user then waits for a short period of time to determine whether the medicament has had the desired effect. If no effect is achieved then the delivery means 5 can be repositioned and the delivery device operated again in the same manner. Likewise, if insufficient effect is achieved from the delivered medicament, then, with the delivery means 5 in the same position, the user operates the delivery device again. When the desired effect has been achieved, the user withdraws the delivery means 5 and fits the sheath 41 thereto. The delivery device can then either be thrown away or stored until required again if there are unused doses or it is to be reused.

Figure 18:
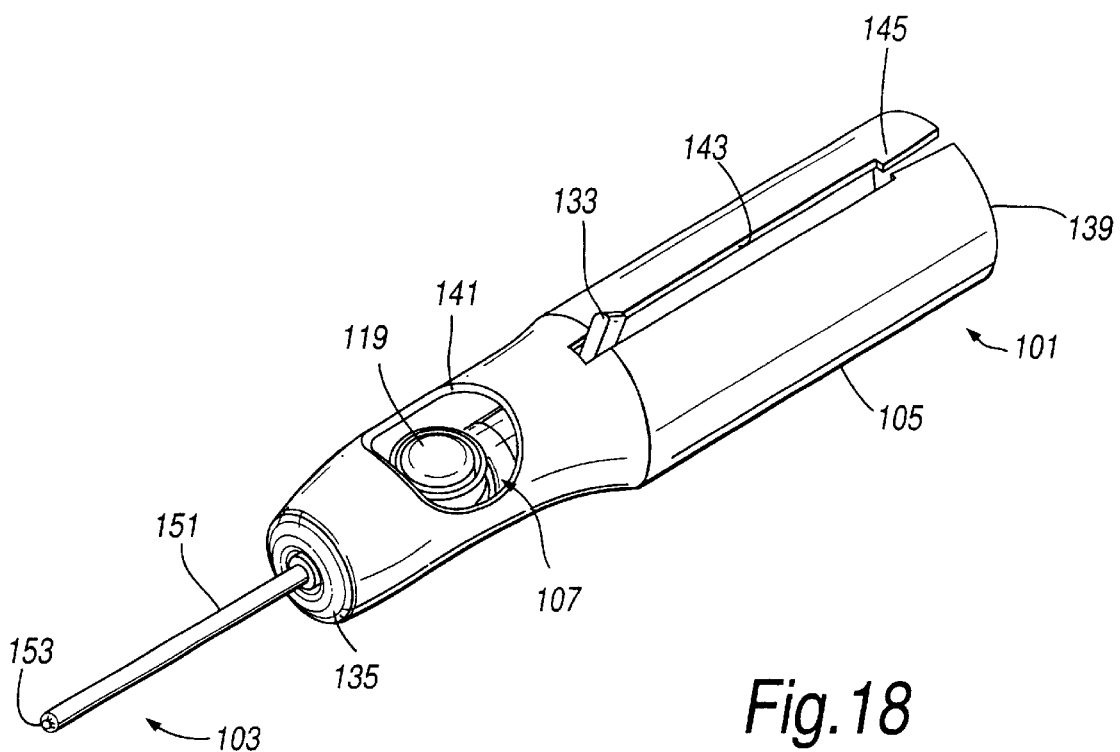
FIG. 18 illustrates a perspective view of a second delivery device in the in use position incorporating a delivery means in accordance with an eleventh embodiment of the present invention.

FIG. 18 illustrates a second delivery device which comprises a delivery unit 101 and a delivery means 103 in accordance with an eleventh embodiment of the present invention from which liquid is in use delivered.

The delivery unit 101 comprises an elongate tubular housing 105 and a pump assembly 107 slideably disposed there within. In this embodiment the housing 105 and the pump assembly 107 are formed of plastics materials, preferably polyethylene or polypropylene.

The pump assembly 107 comprises a main body 109 which defines a chamber 111 having a first opening 113 which defines an inlet, a second opening 115 which defines an outlet and a third opening 117 across which a resilient membrane 119 is disposed. The resilient membrane 119, in this embodiment convex in shape, forms a part of the wall of the chamber 111 and includes a peripheral bead 121 by which the membrane 119 is attached to the main body 109. The first opening 113 includes a one-way valve 123, in this embodiment a flap valve, which allows liquid to flow into the chamber 111 but not out of the chamber 111, and a hollow needle 125 to which a container 127 is in use attached as will be described hereinbelow. The second opening 115 includes a one-way valve 129, which allows liquid to flow out of the chamber 111 but not into the chamber 111, and a tubular section 131 for receiving one end of the delivery means 103 as will be described hereinbelow.

The pump assembly 107 further comprises a projection 133, in this embodiment in the form of a knob, which can be acted upon by a finger or thumb of a user to slide the pump assembly 107 in the housing 105 between the extended in use position as illustrated in FIGS. 18 to 20 and the retracted storage position as illustrated in FIG. 21.

The housing 105 has an end member 135 in which a small opening 137 is formed through which the delivery means 103 passes in use. The other end 139 of the housing 105 is open to allow for the insertion and removal of the pump assembly 107. The housing 105 also includes a lateral opening 141 near the end member 135 thereof at which the membrane 119 of the pump assembly 107 is located when the pump assembly 107 is in the extended in use position as illustrated in FIGS. 18 to 20. In this extended position the pump assembly 107 can be actuated by depressing the membrane 119 as will be described hereinbelow. The housing 105 further includes a longitudinal slot 143, which extends from the open end 139 thereof to a position near the lateral opening 141, in which the projection 133 on the pump assembly 107 is slideably disposed. In this embodiment the end of the longitudinal slot 143 at the open end 139 of the housing 105 includes a restriction 145 which acts as a catch beyond which the projection 133 on the pump assembly 107 cannot pass without first splaying open the longitudinal slot 143 at the open end 139 of the housing 105. In this way, when a user retracts the delivery means 103, the pump assembly 107 cannot be accidentally withdrawn from the housing 105.

The delivery unit 101 further comprises a container 127. The container 127 is of the same construction as that employed in the above-described first delivery device and comprises a first, rigid hemi-spherical part 127a, a second, shank part 127b, which extends axially from the first part 127a and has an elongate bore 147 that is configured to receive the hollow needle 125 at the first opening 113 of the pump assembly 107, and a third, deformable hemi-spherical part 127c, which with the first part 127a defines a spherical chamber 149 that contains a volume of liquid for delivery. In a reusable delivery device a used container 127 can be removed and replaced by a new container 127. The material of the container 127 is selected according to the contained liquid; it being necessary for the material to be inert to the contained liquid. Typical materials include polyethylene and polypropylene. In this embodiment, prior to fitting, the distal end of the shank part 127b of the container 127 is closed by a film (not illustrated), preferably of a plastics material such as polyethylene or polypropylene, which acts to enclose the liquid in the container 127. In use, the third part 127c of the container 127 is configured to collapse as liquid is withdrawn from the container 127.

Figure 22:
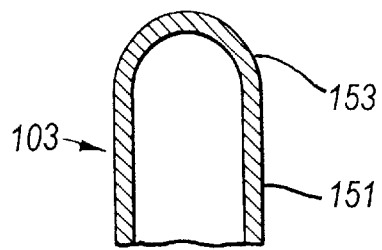
FIG. 22 illustrates in enlarged scale a diametric sectional view (along section E—E in FIG. 23) of the distal end of the delivery means of the delivery device of FIG. 18.
Figure 23:
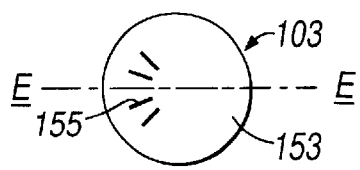
FIG. 23 illustrates an end view of the distal end of the delivery means of FIG. 22.

The delivery means 103 comprises an elongate tubular member 151 and a nozzle 153 at the distal end thereof, which nozzle 153 includes a plurality of openings 155 arranged to eject liquid therefrom in a focused pattern. As illustrated in FIGS. 22 and 23, in this embodiment the nozzle 153 is integrally formed with the tubular member 151 and the openings 155 are radially-directed slits. In practice the nozzle 153 is formed by melting the end of the tubular member 151 so as to provide a closed part-spherical surface and then providing a plurality of openings 155 therein. In a preferred embodiment the tubular member 151 is flexible and comprises one of polyethylene or polypropylene. The tubular member 151 preferably has a length of about 40 mm, an outer diameter of from 1 to 2 mm and a wall thickness of about 0.1 mm.

Figure 24:
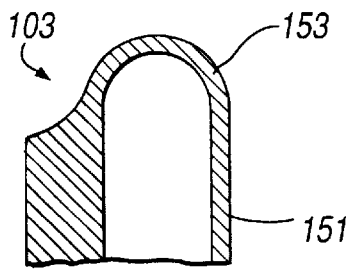
FIG. 24 illustrates in enlarged scale a diametric sectional view (along section F—F in FIG. 25) of the distal end of a delivery means in accordance with a twelfth embodiment of the present invention.
Figure 25:
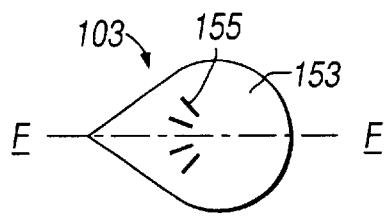
FIG. 25 illustrates an end view of the distal end of the delivery means of FIG. 24.

FIGS. 24 and 25 illustrate the distal end of a delivery means 103 in accordance with a twelfth embodiment of the present invention. In this embodiment the tubular member 151 is of the same general construction as that of the above-described eleventh embodiment, but is asymmetric in shape. This asymmetric shape serves two functions, these being to allow the tubular member 151 to be attached to the delivery unit 101 with a particular angular relationship, which is important where the openings 155 in the nozzle 153 are provided to only one side, and also to indicate the direction in which liquid will in use be ejected from the openings 155 in the nozzle 153.

In use, the user takes the delivery device loaded typically with a local anaesthetic, such as Xylocaine®, as illustrated in FIG. 21 and with a finger or thumb acts on the projection 133 on the pump assembly 107 to move the delivery means 103 to the extended position as illustrated in FIGS. 18 to 20. The user then primes the delivery device by depressing the membrane 119 of the pump assembly 107 a sufficient number of times to ensure that the chamber 111 of the pump assembly 107 is full of liquid. The user then further wets the hydrophilic coating on the tubular member 151 of the delivery means 103 and passes the same into one of his/her nasal passages. The distal end of the delivery means 103, which includes the nozzle 153, is located typically adjacent a posterior region of the nasal cavity. Where the nozzle 153 includes openings 155 on only one side, the user ensures that side of the nozzle 153 in which the openings 155 are located is directed towards the site to which liquid is to be applied. In the embodiment of FIGS. 24 and 25 this is achieved by directing the elongate part of the asymmetric tubular member 151 of the delivery means 103 in the direction in which liquid is to be ejected. When the delivery means 103 is fully inserted, the user then actuates the pump assembly 107 by depressing the membrane 119 to eject a metered volume of liquid from the delivery means 103. In depressing the membrane 119 a positive pressure develops in the chamber 111 which opens the outlet valve 129 allowing liquid to leave the chamber 111 and closes the inlet valve 123. On releasing the membrane 119 a reduced pressure develops in the chamber 111 causing the outlet valve 129 to close and the inlet valve 123 to open through which liquid is drawn from the container 127 until the membrane 119 returns to the original position. In this way, the chamber 111 is filled with a metered volume of liquid which would be ejected from the delivery means 103 on a further actuation of the pump assembly 107. In preferred embodiments the pump assembly 107 is configured such that on each actuation thereof a volume of liquid of from 100 to 250 μl is ejected from the delivery means 5. After actuating the pump assembly 107 the user then waits for a short period of time to determine whether the medicament has had the desired effect. If no effect is achieved then the delivery means 103 can be repositioned and the delivery device operated again in the same manner. Likewise, if insufficient effect is achieved from the delivered medicament, then, with the delivery means 103 in the same position, the user operates the delivery device again. When the desired effect has been achieved, the user withdraws the delivery means 103 from the nasal passage and once withdrawn acts on the projection 133 on the pump assembly 107 to retract the delivery means 103 into the housing 105. The delivery device can then either be thrown away or stored until required again if there are unused doses or it is to be reused.

Finally, it will be understood that the present invention is not limited to the described embodiments but can be modified in many different ways without departing from the scope of the appended claims.

What is claimed is:

1. A delivery device for delivering one or more metered volumes of liquid containing medicament to a posterior region of the nasal cavity, comprising a delivery means (103) as an elongate tubular member (151) and a nozzle (153) at the free end thereof, through which liquid containing medicament is delivered, and a delivery unit (101) coupled to the delivery means (103), the delivery unit (101) comprising a pump assembly (107) on the actuation of which a metered volume of liquid is delivered to the delivery means (103), characterized in that the pump assembly (107) comprises a main body (109) which defines a chamber (111) having a first opening (113) that defines an inlet, a second opening (115) that defines an outlet and a third opening across which a resilient membrane (119) is disposed whereby delivery of a metered volume of liquid to the outlet is achieved by movement of the membrane, and wherein said delivery unit (101) further comprises a housing (105) in which the delivery means (103) and the pump assembly (107) are slideably disposed, wherein the delivery means (103) is movable between a first position in which the delivery means (103) is substantially within the housing (105) and a second position in which the delivery means (103) is extended from the housing (105) in a position ready for use.

2. The delivery device according to claim 1, characterized in that the housing (105) includes a longitudinal slot (143) and the pump assembly (107) includes a projection (133) which extends through the slot (143) for providing the user with a means for slideably positioning the delivery means (103).

3. A delivery device according to claim 2, characterized in that the delivery unit (101) further comprises a container (127), at least a part (127c) of which is deformable, for holding a volume of liquid, which container (127) collapses on delivery of liquid.

4. A delivery device according to claim 3, characterized in that the nozzle (153) includes at least one opening (155) through which liquid is delivered.

5. A delivery device according to claim 4, characterized in that said opening (155) is radially-directed.

6. A delivery device according to claim 4, characterized in that said opening (155) is circularly-directed.

7. A delivery device according to claim 4, characterized in that said opening (155) is located at the periphery of the nozzle (153).

8. A delivery device according to claim 4, characterized in that said opening (155) is located on a circle whose radius is smaller than that of the radius of the nozzle (153).

9. A delivery device according to claim 8, characterized in that said opening (155) is circular.

10. A delivery device according to claim 8, characterized in that said opening (155) is polygonal.

11. A delivery device according to claim 4, characterized in that said opening (155) is elongate.

12. A delivery device according to claim 11, characterized in that said opening (155) is linear.

13. A delivery device according to claim 12, characterized in that said opening (155) comprises a slit.

14. A delivery device according to claim 12, characterized in that said opening (155) comprises a slot.

15. A delivery device according to claim 11, characterized in that said opening (155) is arcuate.

16. A delivery device according to any one of claims 4–15 characterized in that said nozzle (153) comprises a plurality of openings (155) through which liquid is delivered.

17. A delivery device according to claim 16, characterized in that said openings (155) are located on at least two circles having different radii.

18. A delivery device according to claim 17, characterized in that said tubular member (151) and said nozzle (153) are integrally formed.

19. A delivery device according to claim 18, characterized in that said distal end of said nozzle (153) is part-spherical.

20. A delivery device according to claim 4, characterized in that said tubular member (151) is flexible.

21. A delivery device according to claim 4, characterized in that said tubular member (151) includes a hydrophilic coating.

22. A delivery device according to claim 4, characterized in that said tubular member (151) is asymmetric in cross-section.

* * * * *